(12) United States Patent
Otomaru et al.

(10) Patent No.: US 11,557,039 B2
(45) Date of Patent: Jan. 17, 2023

(54) IMAGE PROCESSING APPARATUS, METHOD FOR CONTROLLING IMAGE PROCESSING APPARATUS, AND NON-TRANSITORY COMPUTER-READABLE STORAGE MEDIUM

(71) Applicant: CANON KABUSHIKI KAISHA, Tokyo (JP)

(72) Inventors: Itaru Otomaru, Kanagawa (JP); Toshimizu Yamane, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 8 days.

(21) Appl. No.: 17/061,030

(22) Filed: Oct. 1, 2020

(65) Prior Publication Data
US 2021/0019888 A1 Jan. 21, 2021

Related U.S. Application Data

(63) Continuation of application No. PCT/JP2019/015074, filed on Apr. 5, 2019.

(30) Foreign Application Priority Data

Apr. 12, 2018 (JP) .............................. JP2018-077138

(51) Int. Cl.
*G06K 9/00* (2022.01)
*G06T 7/00* (2017.01)
(Continued)

(52) U.S. Cl.
CPC .......... *G06T 7/0016* (2013.01); *A61B 5/7425* (2013.01); *G06F 3/14* (2013.01);
(Continued)

(58) Field of Classification Search
CPC ......... G06T 7/0016; G06T 2207/10081; G06T 2207/10088; G06T 2207/10101;
(Continued)

(56) References Cited

U.S. PATENT DOCUMENTS

2006/0238546 A1* 10/2006 Handley ............ H04N 1/00442
382/128
2007/0242069 A1* 10/2007 Matsue .................. G16H 30/40
345/428
(Continued)

FOREIGN PATENT DOCUMENTS

JP 2007-282656 A 11/2007
JP 2008-173213 A 7/2008
(Continued)

OTHER PUBLICATIONS

Beg, et al. "Computing Large Deformation Metric Mappings via Geodesic Flows of Diffeomorphisms", International Journal of Computer Vision 61 (2), Feb. 2005.

*Primary Examiner* — Atiba O Fitzpatrick
(74) *Attorney, Agent, or Firm* — Canon U.S.A., Inc. IP Division

(57) ABSTRACT

An image processing apparatus selects one or a plurality of examinations to which a medical image belongs, determines image processing candidate examinations based on the selected one or plurality of examinations, displays medical images belonging to the determined image processing candidate examinations on a display unit, and executes image processing using, of the displayed medical images, a plurality of medical images selected by a user, wherein, when the one examination is selected, the selected one examination and one or a plurality of examinations obtained by a search based on the selected one examination are determined as the image processing candidate examinations, and when the plurality of examinations are selected, in the determining, the selected plurality of examinations are determined as the image processing candidate examinations.

10 Claims, 6 Drawing Sheets

(51) Int. Cl.
*A61B 5/00* (2006.01)
*G06F 3/14* (2006.01)

(52) U.S. Cl.
CPC ............... *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/10136* (2013.01); *G06T 2207/30004* (2013.01)

(58) Field of Classification Search
CPC . G06T 2207/10104; G06T 2207/10108; G06T 2207/10136; G06T 2207/30004; G06T 7/0014–0016; G06T 7/30–38; G06T 2219/2004; A61B 5/7425; A61B 2090/364; G06F 3/14; G06F 3/0484–04845; G06F 3/0486; G06F 3/04886; G06V 40/167; G06V 10/759; G06V 30/19013
See application file for complete search history.

(56) References Cited

U.S. PATENT DOCUMENTS

2013/0088512 A1* 4/2013 Suzuki .................. G16H 10/60
    345/629
2019/0096072 A1* 3/2019 Sasada ....................... G06T 7/38

FOREIGN PATENT DOCUMENTS

| JP | 2013-128725 A | 7/2013 |
| JP | 2016-035717 A | 3/2016 |
| JP | 2018-033545 A | 3/2018 |
| JP | 2019-058374 A | 4/2019 |

\* cited by examiner

IMAGE PROCESSING APPARATUS, METHOD FOR CONTROLLING IMAGE PROCESSING APPARATUS, AND NON-TRANSITORY COMPUTER-READABLE STORAGE MEDIUM

CROSS-REFERENCE TO RELATED APPLICATIONS

This application is a Continuation of International Patent Application No. PCT/JP2019/015074, filed Apr. 5, 2019, which claims the benefit of Japanese Patent Application No. 2018-077138, filed Apr. 12, 2018, both of which are hereby incorporated by reference herein in their entirety.

BACKGROUND OF THE INVENTION

Field of the Invention

The present invention relates to an image processing apparatus, a method for controlling the image processing apparatus, and a non-transitory computer-readable storage medium.

Background Art

Some medical image processing uses two images of the same subject as an input. Known example image processing emphasizes temporal changes in lesions by calculating the difference between two images of the same subject captured at different times. NPL 1 discloses a method for deformable registration of two images (a set of images). The deformable registration allows for generating a subtraction image in which changes in characteristics between the two images are emphasized.

An issue in the image processing using two images as an input is which of the two images is to be selected. This is because image capturing (examination) of one subject is performed a plurality of times over a given period (several months to several years), and a plurality of images are captured at one examination. For this reason, the operator needs to select two images from the large number of images. PTL 1 discloses a technique for searching past images of the identical patient using the patient ID of the currently selected image as a key.

CITATION LIST

Patent Literature

PTL 1 Japanese Patent Laid-Open No. 2008-173213

Non Patent Literature

NPL 1 Mirza et al., Computing Large Deformation Metric Mappings via Geodesic Flows of Diffeomorphisms, International Journal of Computer Vision, 61(2), 139-157, 2005.

However, with the related art, it was not possible to easily select images according to the operator's intention.

SUMMARY OF THE INVENTION

An image processing apparatus according to the present invention has the following configuration. The image processing apparatus comprises a selection unit configured to select one or a plurality of examinations to which a medical image belongs, a determination unit configured to determine image processing candidate examinations based on the selected one or plurality of examinations, a display control unit configured to display medical images belonging to the determined image processing candidate examinations on a display unit, and an image processing unit configured to execute image processing using, of the displayed medical images, a plurality of medical images selected by a user. When the one examination is selected, the determination unit determines the selected one examination and one or a plurality of examinations obtained by a search based on the selected one examination as the image processing candidate examinations, and when the plurality of examinations are selected, the determination unit determines the selected plurality of examinations as the image processing candidate examinations.

Further features of the present invention will become apparent from the following description of exemplary embodiments (with reference to the attached drawings).

DESCRIPTION OF THE EMBODIMENTS

Figure 1:
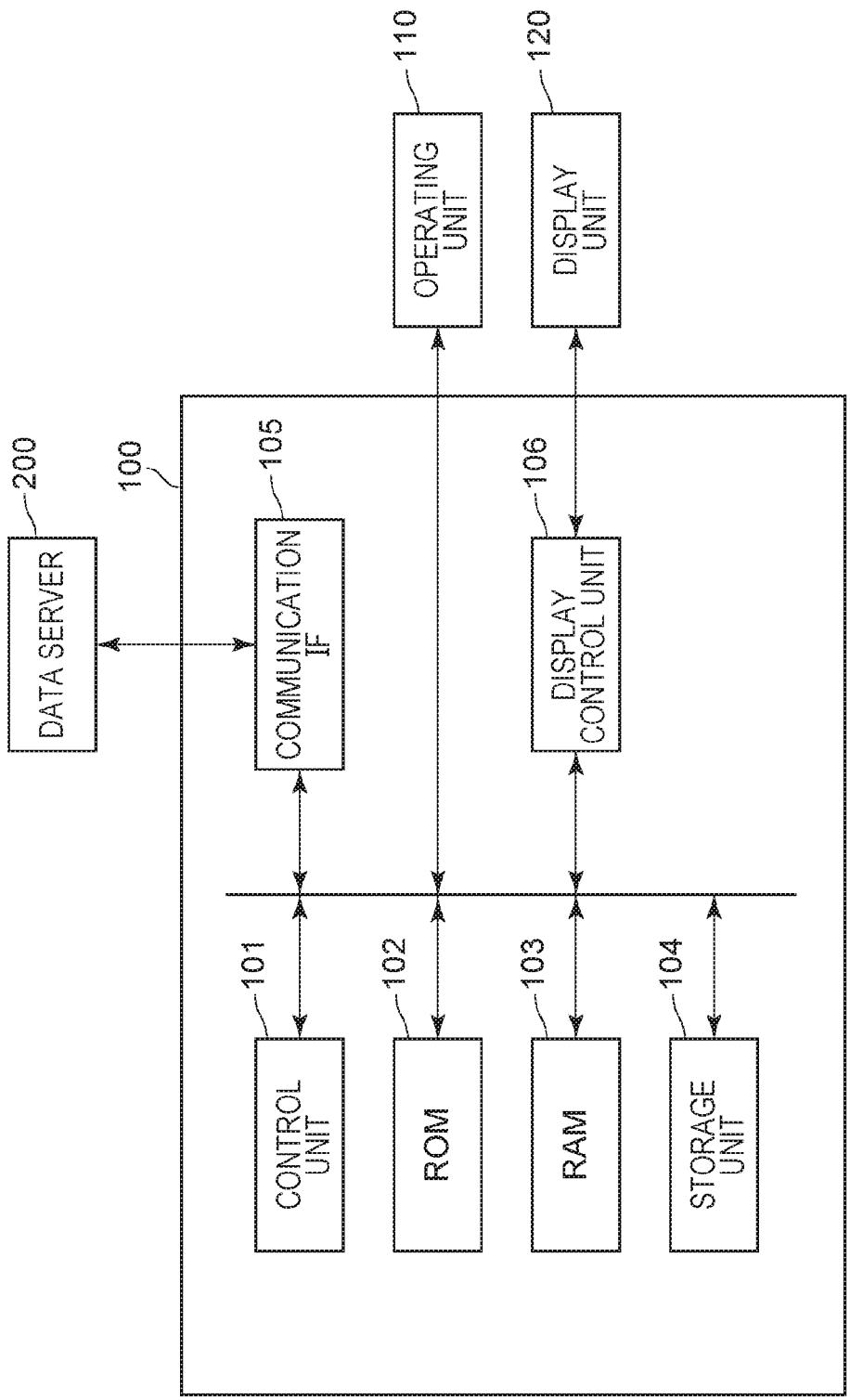
FIG. 1 is a diagram illustrating the hardware configuration of an image processing apparatus according to a first embodiment.

Preferable embodiments of an image processing apparatus according to the present invention will be described in detail hereinbelow with reference to the accompanying drawings. However, the scope of the present invention is not limited to the illustrations.

First Embodiment

An image processing apparatus according to the present embodiment changes the image selection screen according to the number of examinations that the operator (user) selects. If the number of examinations that the operator selects is one, the image processing apparatus searches a data server to obtain candidates of examinations to be subjected to image processing (hereinafter referred to as processing candidate examinations) and reflects the examinations in the image selection screen. In contrast, if the number of examinations that the operator selects is two or more, no search is performed, and information on the selected examination group is reflected in the image selection screen as it is, as processing candidate examinations. Thereafter, two images to be subjected to image processing are selected by the operator from images that belong to the processing candidate examinations using the image selection screen. Then, the image processing apparatus executes predetermined image processing using the images narrowed down to two as an input.

Here, the relationship between "examination" and "image" in the present embodiment will be described in detail. In general, a plurality of image capturing operations are performed at one examination, as described above. Here, each image at that time is referred to as "image" (corresponding to a medical image), and the images captured at one examination are collectively referred to as "examinations". The "examinations" and "image" are respectively the same concepts as those of "study" and "series" in the Digital Imaging and Communications in Medicine (DICOM) standard. The image processing apparatus receives an input of "examinations" (group) selected by the operator, as described in the preceding paragraph. Then, two "images" to be subjected to image processing are selected from the "examinations" (group) by the selection of the operator using the image selection screen provided by the image processing apparatus.

The present embodiment is described using an example in which three-dimensional X-ray computed tomography (CT) images are the target. However, the application range of the present invention is not limited to the three-dimensional X-ray CT images. For example, a two-dimensional image, such as a simple X-ray image or an ultrasonic (US) image, may be used, or one of two images for use in image processing may be a two-dimensional image and the other may be a three-dimensional image. The three-dimensional images are not limited to the X-ray CT images but may be any images, such as a magnetic resonance image (MRI), a three-dimensional US image, an optical ultrasonic tomography image, a positron emission tomography/single photon emission tomography (PET/SPECT) image, and an optical coherence tomography (OCT) image.

Referring to FIGS. 1 to 4, the configuration and processing of the present embodiment will be described hereinbelow.

FIG. 1 illustrates an example of the hardware configuration of an image processing apparatus 100 according to the present embodiment. The hardware configuration of the image processing apparatus 100 illustrated in FIG. 1 is a mere example and is not intended to limit the present invention.

The image processing apparatus 100 includes a control unit 101, a read only memory (ROM) 102, a random access memory (RAM) 103, a storage unit 104, a communication interface (communication IF) 105, and a display control unit 106. The hardware is connected to a system bus. The image processing apparatus 100 connects to an operating unit 110 and a display unit 120. Each of the hardware components need to be at least one. The image processing apparatus 100 also connects to a data server 200 via the communication IF 105.

An example of the control unit 101 is a processor, such as a central processing unit (CPU), which controls the individual hardware components connected to the system bus as a whole. The ROM 102 is a non-volatile memory or the like and stores various programs. The RAM 103 is hardware, such as a volatile memory, serving as the main memory and the work area of the control unit 101 to temporarily store various pieces of information as data. Examples of the storage unit 104 include a hard disk drive (HDD) and a solid state drive (SSD). An example of the communication IF 105 is a local area network (LAN) card, which establishes communication between an external apparatus (for example, a data server) and the image processing apparatus 100 via a network. The display control unit 106 is a control unit that causes the display unit 120 to display various pieces of information. The display control unit 106 corresponds to, for example, a graphic controller (GPU etc.). The display control unit 106 may be omitted, and the function of the display control unit 106 may be provided to the control unit 101.

The operating unit 110 is a device, such as a keyboard, a mouse, or a touch panel, for inputting instructions from the operator to the image processing apparatus 100. The display unit 120 is a display (for example, a liquid-crystal display) for displaying various kinds of information indicated by the display control unit 106.

Various programs and so on for the image processing apparatus 100 of the present invention to use in executing various processes are stored in the storage unit 104, are loaded to the RAM 103 as necessary, and are executed by the control unit 101. definition files and various information tables that the programs of the present invention use are stored in the storage unit 104.

Although FIG. 1 illustrates an example in which the data server 200 is an apparatus separate from the image processing apparatus 100, part of the storage unit 104 may be assigned as a data server. Although FIG. 1 illustrates an example in which the image processing apparatus 100 is a single apparatus, any hardware resource, such as the control unit 101 or the storage unit 104, may be used using cloud computing via the Internet.

Figure 2:
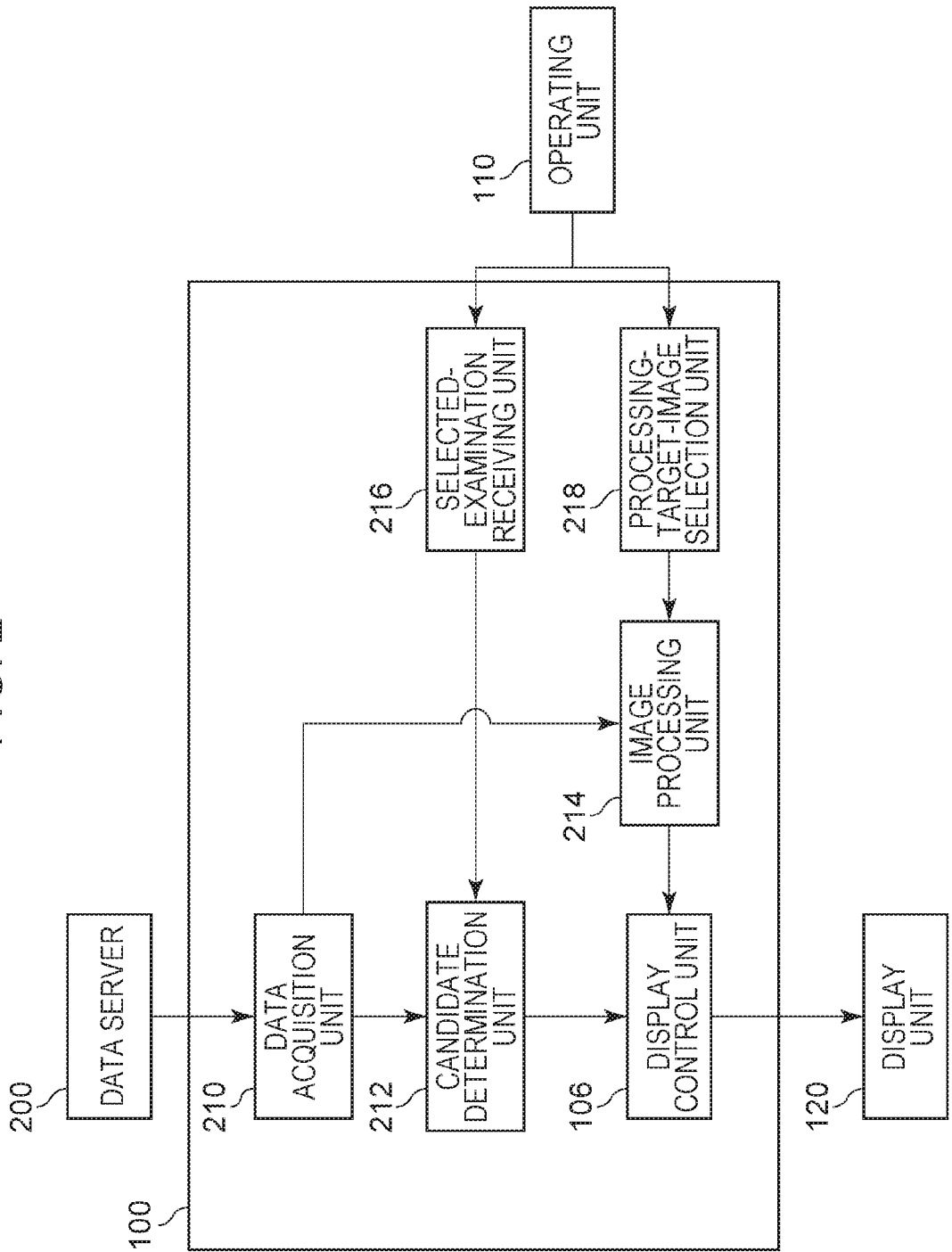
FIG. 2 is a diagram illustrating the configuration of the image processing apparatus according to the first embodiment.

FIG. 2 illustrates an example of the system configuration of the image processing system and the functional configuration of the image processing apparatus 100 according to the present embodiment. The configurations illustrated in FIG. 2 are mere examples and are not intended to limit the present invention. As illustrated in the drawing, the image processing apparatus 100 of the present embodiment is connected to the data server 200, the operating unit 110, and the display unit 120.

The data server 200 stores information on all examinations that may be subjected to image processing by the image processing apparatus 100 and information on all images that belong to the examinations. The individual images included in the examinations are three-dimensional images that are configured as a set of two-dimensional tomographic images. The positions and orientations of the two-dimensional tomographic images are stored in the data server 200 after being converted to a reference coordinate system (a coordinate system in space based on the subject). The examination information and image information stored in the data server 200 are input to the image processing apparatus 100 via the data acquisition unit 210.

The operating unit 110 receives a manipulated input, such as depression of a mouse, a keyboard, or a touch panel, by the operator and inputs various kinds of information to the image processing apparatus 100 via the selected-examination receiving unit 216 or the processing-target-image selection unit 218.

The display unit 120 displays an image selection screen or a processing result image that the image processing apparatus 100 generates. The image selection screen is a graphical user interface (GUI) that lists information on all images included in the examination group for the user to select two images for use in image processing. The processing result image is a three-dimensional image, and when displayed on the display unit 120, it is a two-dimensional tomographic image selected by the operator. The display unit 120 also displays a GUI for obtaining various instructions from the operator, such as starting image processing.

The image processing apparatus 100 includes the following components. A data acquisition unit 210 obtains examination information and image information from the data server 200. A selected-examination receiving unit 216 receives the information on examination selected by the operator and obtain it. A candidate determination unit 212 determines processing candidate examinations on the basis of the information on the examination selected by the operator and obtain it. A processing-target-image selection unit 218 obtains two images to be processed from the processing candidate examinations on the basis of the selection by the operator. An image processing unit 214 executes predetermined image processing on the two images selected by the operator. The display control unit 106 obtains information from the candidate determination unit 212 and the image processing unit 214 and displays the image selection screen or the processing result image on the display unit 120.

Figure 3:
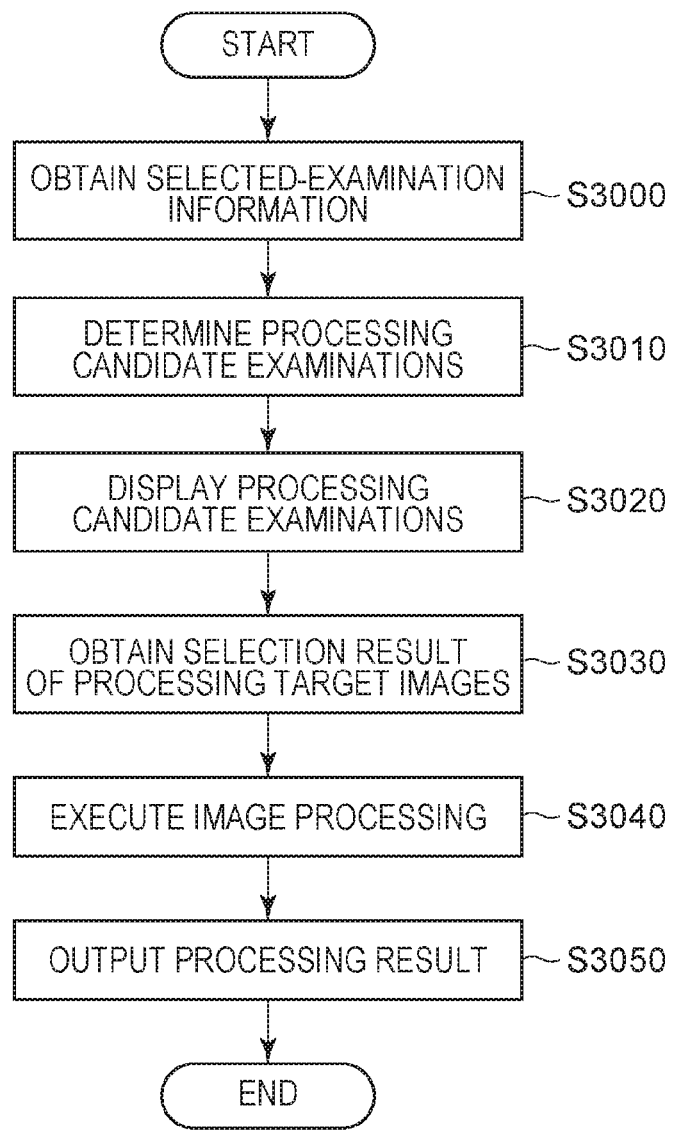
FIG. 3 is a flowchart illustrating the overall processing procedure in the first embodiment.

FIG. 3 is a flowchart illustrating the overall processing procedure of the image processing apparatus 100.

(S3000) (Obtaining Selected-Examination Information)

In step S3000, the selected-examination receiving unit 216 receives information on an examination (group) selected by the operator to obtain it. In other words, the selected-examination receiving unit 216 corresponds to an example of the selection unit that selects one or a plurality of examinations to which the medical image belongs. The number of examinations (group) that the operator selects is any number equal to or greater than 1. Information on the selected examination (group) (for example, examination ID) is temporarily stored in the RAM 103 in the image processing apparatus 100.

The selection of examination can be performed by the operator, for example, from an examination list displayed on the selection screen (not illustrated) using a GUI, or by the operator inputting the examination ID.

(S3010) (Determining Processing Candidate Examinations)

In step S3010, the candidate determination unit 212 determines processing candidate examinations using the examination selection information obtained in step S3000. In other words, the candidate determination unit 212 corresponds to an example of the determination unit that determines image processing candidate examinations on the basis of the selected one or plurality of examinations. The information indicating the determined processing candidate examinations (for example, examination IDs) is input to the display control unit 106.

A method for determining processing candidate examinations will be specifically described. The method for determining processing candidate examinations changes depending on whether the number of examinations (group) selected by the operator in step S3000 is one or two or more. Specifically, if the number of selected examinations is two or more, the candidate determination unit 212 determines the examination group selected by the operator as processing candidate examinations as they are. In contrast, if the number of selected examinations is one, the candidate determination unit 212 determines processing candidate examinations by searching the data server 200 on the basis of the selected examination. In other words, the candidate determination unit 212 corresponds to an example of the determination unit characterized by, when one examination is selected, determining the selected one examination and one or a plurality of examinations obtained by a search based on the selected one examination as image processing candidate examinations. The candidate determination unit 212 also corresponds to an example of the determination unit characterized by, when a plurality of examinations are selected, determining the selected plurality of examinations as image processing candidate examinations.

The processing for searching the data server 200 to determine processing candidate examinations is performed according to the following procedure. First, the candidate determination unit 212 obtains examination attribute information (additional information) from the examination selected by the operator. The examination attribute information includes patient ID, modality type, and target site. The candidate determination unit 212 determines an examination (group) that matches the examination whose attribute information is selected as a processing candidate examination by searching the data server 200 using the attribute information as a key. The attribute information serving as the search key is one of patient ID, modality type, and target site or a combination of a plurality of pieces of attribute information, such as "patient ID and modality type". This allows the candidate determination unit 212 to obtain an examination group whose attribute information on the examination selected by the operator is the same.

A method for searching is not limited to the above methods but may be any searching method suitable for image processing that the image processing unit 214 executes. For example, in the case where the image processing is an image registration between different modalities, a search condition "a modality type different from that of examination(s) selected by the operator" may be employed. In other words, if the modality of the examination selected by the operator is CT, the candidate determination unit 212 searches for an examination whose modality type is MRI.

(S3020) (Displaying Processing Candidate Examinations)

In step S3020, the display control unit 106 performs control to display information on the processing candidate examinations determined in step S3010 on the display unit 120. In other words, the display control unit 106 corresponds to an example of the display control unit that displays medical images that belong to the determined image processing candidate examinations on the display unit.

Figure 4:
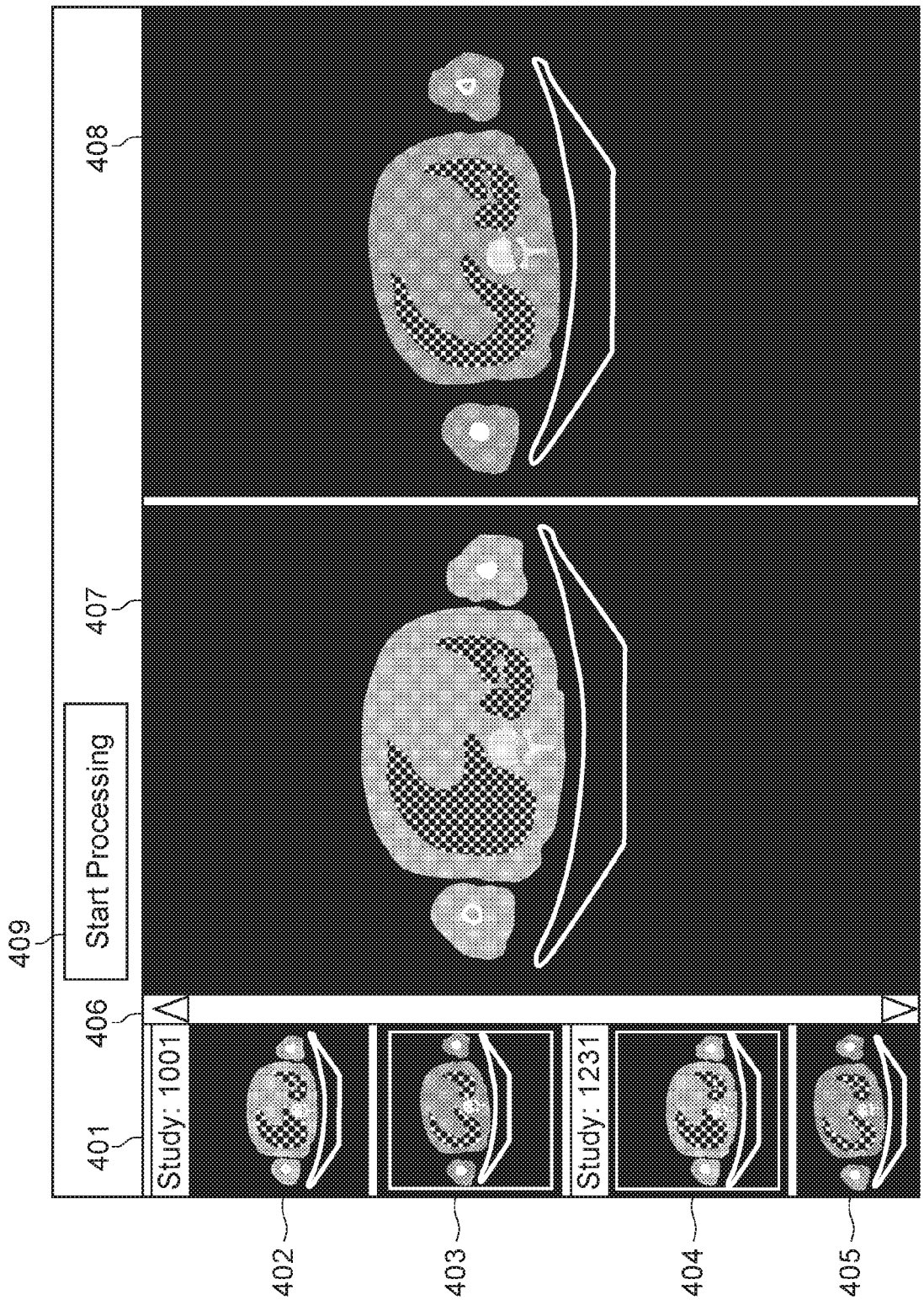
FIG. 4 is a diagram illustrating an example of an image selection user interface in the first embodiment.

Referring to FIG. 4, an example of the display form of an image group will be described. FIG. 4 is an example of the image selection screen. A thumbnail display area 401 at the left of FIG. 4 displays the thumbnails of an image group included in the processing candidate examinations obtained in step S3010. Here, two examinations "Study: 1001" and "Study: 1231" are calculated as processing candidate examinations, each of which has two images 402 and 403 and two images 404 and 405. If the thumbnails of the image group are not fit in one screen, the thumbnails can be moved outside the screen by operating a scroll bar 406.

In the example image group display form illustrated in FIG. 4, not only the thumbnails of the images described above but also any image can be selected so that the image can be observed in more detail. In this case, the operator drags and drops any one of thumbnails 402, 403, 404, and 405 with a mouse into a detailed-image display area 407 or 408. When the instruction is input, the display control unit 106 reads a three-dimensional image corresponding to the selected thumbnail and displays it in the detailed display area. The image displayed in the detailed display area can be observed in detail using various image-observation assisting functions, such as slice feeding, changing the window width or window level, and changing the magnification ratio.

Although the present embodiment has been described using an example in which a list of image group is presented as thumbnail images, of which any image is dragged and dropped with a mouse for detailed observation, another display form or operation form may be employed. For example, not the thumbnail display but a character string indicating image attribute information, such as image capturing date and time or the number of slices, may be displayed, or a combination of thumbnail display and character string display may be employed. Not the drag-and-drop operation with a mouse but a keyboard or a touch panel may be used to perform an equivalent operation.

(S3030) (Obtaining Selection Result of Processing Target Images)

In step S3030, the processing-target-image selection unit 218 obtains a processing-target-image selection result input by the operator. The processing-target-image selection result is the result of selection of two images (processing target images) to be input for image processing. The input of the selection result by the operator is performed on the image selection screen generated in step S3020.

An example of a method for obtaining the processing target image selection result will be described with reference to FIG. 4. As described in step S3020, the thumbnails of all examinations and all images which are processing target candidates are displayed at the left (401) of the display screen. Dragging and dropping any thumbnail to the detailed-image display area 407 or 408 allows the image to be observed in detail.

On the above display screen, the operator searches for two images suitable for image processing while repeating the drag and drop of the thumbnails and detailed observation of the images by trial and error. When two images for use in image processing are determined, the operator presses "Start Processing" button (409). When the button is pressed, the processing-target-image selection unit 218 obtains the two images read in the detailed-image display areas 407 and 408 as a processing target image selection result. The processing is then shifted to step S3040.

In the case where the roles of the two images are different in the subsequent image processing (for example, one image is fixed, and the other image is aligned by deformable registration), the operator selects the images in consideration of it. In this case, the processing-target-image selection unit 218 assumes the image specified in the detailed-image display area 407 to be a first input image (hereinafter also referred to as "reference image") and the image specified in the detailed-image display area 408 to be a second input image (hereinafter also referred to as "comparative image").

(S3040) (Executing Image Processing)

In step S3040, the image processing unit 214 executes predetermined image processing using the two images selected in step S3030 as an input. In other words, the image processing unit 214 corresponds to an example of the image processing unit that executes image processing using a plurality of medical images selected from the displayed medical images by the user.

In the present embodiment, "image subtraction" is performed as image processing in which two images are aligned by deformable registration using the technique disclosed in NPT 1 and then the difference between the images is calculated to generate a subtraction image. In this case, the result of image processing is a three-dimensional image (subtraction image). In general, the images are aligned by deforming the comparative image, with the reference image fixed, and thereafter a subtraction image is generated in the same space as that of the reference image. The image processing may be any processing, suitable for the object of the image processing apparatus, that uses two images as an input. For example, bonding (stitching) overlapping areas and super-resolution image processing that restores a high-resolution image from two similar images may be used. The image processing may be performed between images of different modalities. An example is an image registration between a functional image, such as a PET image, and a structural image, such as a CT image, and superposing functional information on the structural image (fusing processing). Another example is an image registration between a CT image and an MRI image to generate an image in which a bone area which is well visualized in the CT image and a muscle area which is well visualized in the MRI image can be observed at the same time.

(S3050) (Outputting Processing Result)

In step S3050, the image processing unit 214 temporarily writes the image processing result (processing result image) calculated in step S3040 into the RAM 103 for image display and registers the image processing result with the data server 200. In this step, the display control unit 106 performs control so that the display unit 120 displays the image processing result. In this case, the display control unit 106 displays the image processing result in a display area in which the detailed-image display areas 407 and 408 in FIG. 4 are connected. Not both of the storage and display of the image processing result need to be performed, only the display or only the storage may be performed.

The processing of the image processing apparatus 100 is performed in that manner.

The present embodiment allows for selecting a suitable image that reflects the operator's intention in selecting an image processing target image. In other words, if the number of examinations selected by the operator in advance is only one, a rough policy, such as "who is to be the target patient of image processing", is determined, but no target examination has been determined. An example is a case in which the latest examination is the target, but the past examination to be compared with has not been determined. Thus, the image processing apparatus 100 is suitable for searching a data base to present candidates. In contrast, a case in which two or more examinations are selected by the operator indicates that examinations to be subjected to image processing are narrowed down to some extent. An example is a case in which the target examination is the latest examination, and the past examination to be compared with is the preceding examination. For this reason, the image processing apparatus 100 is suitable for presenting image candidates within the input examination group not adding a new candidate. Thus, the advantageous effect of the present embodiment is that user interfaces for image selection can be switched seamlessly according to the operator's intention.

(Modification 1 of First Embodiment)

In the first embodiment, the operator specifies not image(s) but examination(s) in step S3000. However, in step S3000, the operator may specify not examination(s) but image(s) itself. In this case, the sequence of processing in the first embodiment described above is performed, with the specified image regarded as one examination.

Second Embodiment

An image processing apparatus according to the present embodiment provides an image selection screen that better matches the operator's intention, in addition to the function of the image processing apparatus 100 in the first embodiment.

Since the configuration of the image processing apparatus according to the present embodiment is the same as the configuration of the first embodiment (FIGS. 1 to 2), a description thereof will be omitted.

The overall processing procedure of the image processing apparatus 100 according to the present embodiment is the same as that of the first embodiment (FIG. 3). However, the processing details of steps S3000, S3010, S3020, and S3030 differ.

(S3000) (Obtaining Selected-Examination Information)

In step S3000, the selected-examination receiving unit 216 performs the same processing as in the first embodiment to receive information on an examination (group) selected by the operator to obtain it. If the number of selected examinations (group) is two or more, the following processing is performed. In other words, the selected-examination receiving unit 216 assumes the first examination, that is, an examination selected at first, to be "reference examination" (diagnosis target examination), and the second and subsequent selected examinations to be "comparative examination (group)". An image (group) belonging to the reference examination is treated as an image (group) that is a candidate of the first input image (reference image) in the subsequent image processing. An image (group) belonging to the comparative examination (group) is treated as an image (group) that is a candidate of the second input image (comparative image) in the subsequent image processing.

Although the present embodiment is described using an example in which the reference examination and the comparative examination (group) are distinguished according to the order of selection of the examinations, the reference examination and the comparative examination may be explicitly specified by the operator. In this case, the reference examination and the comparative examination can be specified regardless of the order of selection, which allows for providing a more flexible operating form.

(S3010) (Determining Processing Candidate Examinations)

In step S3010, the candidate determination unit 212 determines processing candidate examinations by performing the same processing as in step S3010 of the first embodiment. If the number of examinations (group) selected in step S3000 is one, the following processing is performed. In other words, if the number of examinations (group) selected in step S3000 is one, the candidate determination unit 212 assumes the selected examination to be "reference examination", and the examination (group) obtained from the data server 200 by the processing of this step to be "comparative examination (group)".

Thus, the reference examination and the comparative examination (group) are distinguishably selected by performing the processing of step S3000 and S3010 regardless of whether the number of examinations selected by the operator is one or two or more.

(S3020) (Displaying Processing Candidate Examinations)

In step S3020, the display control unit 106 performs control to display the image group calculated in step S3010 on the display unit 120.

Figure 5:
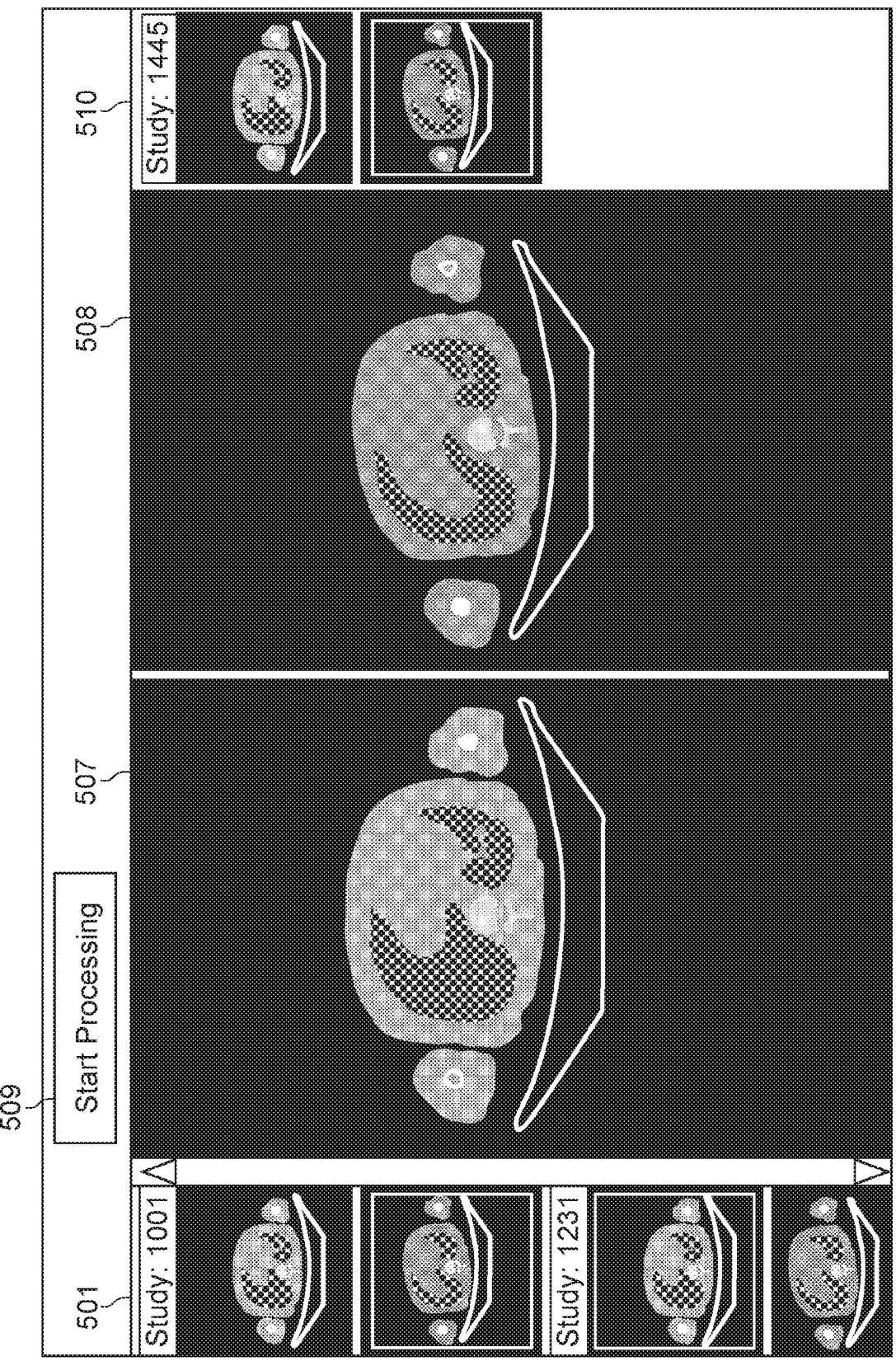
FIG. 5 is a diagram illustrating an example of an image selection user interface in a second embodiment.

Referring to FIG. 5, an example of the display form of the image group will be described. In the case of the first embodiment (FIG. 4), there is no distinction in the processing candidate examinations between a reference examination and a comparative examination, so that all pieces of information on the processing candidate examinations are collectively displayed in a single thumbnail display area (401) at the left of the screen. In contrast, in the present embodiment, the display screen has two thumbnail display areas, a thumbnail display area (501) at the left and a thumbnail display area (510) at the right. The thumbnail display area at the left (a second display area) displays the thumbnails of images belonging to the comparative examination (group), and the thumbnail display area at the right (a first display area) displays the thumbnails of images belong to the reference examination. This allows the operator to clearly distinguish the image (group) belonging to the reference examination and the image (group) belonging to the comparative examination (group). The two thumbnail display areas need not necessarily be located at the right and left of the display screen. A screen configuration is possible in which the thumbnail display area 501 for the comparative examination (group), the detailed-image display area 507 for the comparative examination (group), the thumbnail display area 510 for the reference examination, and the detailed-image display area 508 for the reference examination are arranged in this order from the left to the right. The thumbnail display area may have a configuration in which thumbnails are laterally arranged, and the thumbnail display area 501 is displayed above or below the detailed-image display area 507, and the thumbnail display area 510 is displayed above or below the detailed-image display area 508 in association with each other. Disposing the thumbnail display area and the detailed-image display area associated with each other has an advantage in allowing the operator to intuitively understand the operation.

Here, an example is illustrated in which only the thumbnails of images are displayed as in the first embodiment. However, images may be displayed in the detailed-image display area 507 or 508, if possible. The term "if possible" indicates a case in which only one examination belongs to the reference examination or the comparative examination and the examination includes only one image. For example, when only one image is registered with the reference examination, the first input image (reference image) is uniquely determined without the need for being selected. In this case, not only displaying the thumbnails but also reading an image to the detailed-image display area (507 or 508) in this step allows for reducing the time and labor of the operator.

(S3030) (Obtaining Selection Result of Processing Target Images)

In step S3030, the processing-target-image selection unit 218 obtains the selection result of processing target images input by the operator. As in the first embodiment, the input of the selection result by the operator is made on the image selection screen generated in step S3020. The difference from the first embodiment will be described hereinbelow.

Referring to FIG. 5, an example of a method for obtaining the selection result of the processing target image will be described. As described in step S3020, the thumbnails (510) of the images (group) belonging to the reference examination are displayed at the right of the screen, and the thumbnails (501) of the images (group) belonging to the comparative examination are displayed at the left of the screen. an image is displayed in the detailed-image display area (507 or 508) by dragging and dropping the thumbnail image, as in the first embodiment. However, in the present embodiment, the thumbnails (510) of the images (group) belonging to the reference examination can be dropped only to the detailed-image display area (508) (a third display area) at the right. The thumbnails (501) of the images (group) belonging to the comparative examination can be dropped only to the detailed-image display area (507) at the left (a fourth display area). In the subsequent image processing, the image in the right-hand detailed-image display area (508) is the first input image (reference image), and the image in the left-hand detailed-image display area (507) is the second input image (comparative image). Thus, limiting the area to which the thumbnail images are dropped prevents an error in image specification. The processing of limiting the drop area is not absolutely necessary.

The processing of the image processing apparatus 100 is performed in that manner.

The present embodiment allows the operator to select images clearly distinguishably between the reference examination and the comparative examination (group). This is useful especially when the image processing is "temporal image subtraction" for determining the temporal change difference of the same subject. A typical usage example of the temporal image subtraction is "in capturing an image of a subject, calculating the difference between the subject image (the current image) and an image (a past image) of the same subject at any past time". In this case, an examination to which the current image belongs is the reference examination. In other words, the comparative examination is searched for from examinations to which the past image group belongs, with the reference examination determined. In the present embodiment, the image processing apparatus 100 provides an image selection function suitable for such a case.

(Modification 1 of Second Embodiment)

In the second embodiment, there are two methods for specifying a reference examination and a comparative examination (group): 1. Specification according to the order of specification by the operator (the first is used as the reference examination, and the second and subsequent examinations are used as the comparative examination (group)) and 2. Explicit specification by the operator. Another configuration is possible in which the reference examination and the comparative examination (group) are specified in consideration of "image capturing date and time" which is one of the examination attribute information.

For example, if the number of specified examinations in step S3000 is two or more, the selected-examination receiving unit 216 may determine an examination having latest image capturing date and time (closest to the present date and time) as a reference examination, and the other examinations as a comparative examination (group). This provides a more suitable image selection function in the case where the image processing is temporal image subtraction for obtaining the temporal change difference of the same subject. As described above, a typical example of how temporal image subtraction is used is "calculating the difference between the current image (in other words, the latest captured image) and an image at any past time. This allows, when a plurality of examinations are selected in step S3000, omitting the time and labor for the operator to explicitly specify the reference examination by using the examination having the latest image capturing date and time as the reference examination.

In contrast, if the number of specified examinations is one, the candidate determination unit 212 can determine the examination as the reference examination regardless of the image capturing date and time. In other words, even if an examination having capturing date and time newer (earlier) than the specified examination is picked up as a result of searching, the examination is not switched to the reference examination. In general, if the operator specifies only one examination, the operator intends to use the examination as the reference examination. This allows for selection according to the operator's intention. Of course, even if the number of specified examinations is one, the latest examination obtained as a result of searching may be used as the reference examination.

(Modification 2 of Second Embodiment)

The second embodiment and modification 1 of the second embodiment have been described using an example in which, when the operator specifies a plurality of examinations, the reference examination and the comparative examination are displayed so as to be distinguished by any way. Another configuration is possible in which, when the operator specifies a plurality of examinations, the reference examination and the comparative examination are not distinguished as in the first embodiment, and only when the operator specifies a single examination, the reference examination and the comparative examination are distinguishably displayed.

For example, if the number of examinations specified in step S3000 is two or more, the processing candidate examinations are displayed in S3020 such that the reference examination and the comparative examination are not distinguished like the display form of the first embodiment (FIG. 4). In contrast, if the number of examinations specified in S3000 is one, the processing candidate examinations are displayed in the display form of the second embodiment (FIG. 5).

This provides a suitable user interface for each of a case in which only the reference examination has been determined and a comparative examination is to be searched for and a case in which two images are to be determined from a certain number of processing candidate examinations without distinguishing the reference examination and the comparative examination.

Third Embodiment

The first and second embodiments have been described using an example in which the information obtained in step S3000 is examination information. In contrast, the information obtained by an image processing apparatus according to the present embodiment is not information but "image".

Since the configuration of the image processing apparatus according to the present embodiment is the same as those of the first and second embodiments (FIGS. 1 to 2), a description thereof will be omitted.

Figure 6:
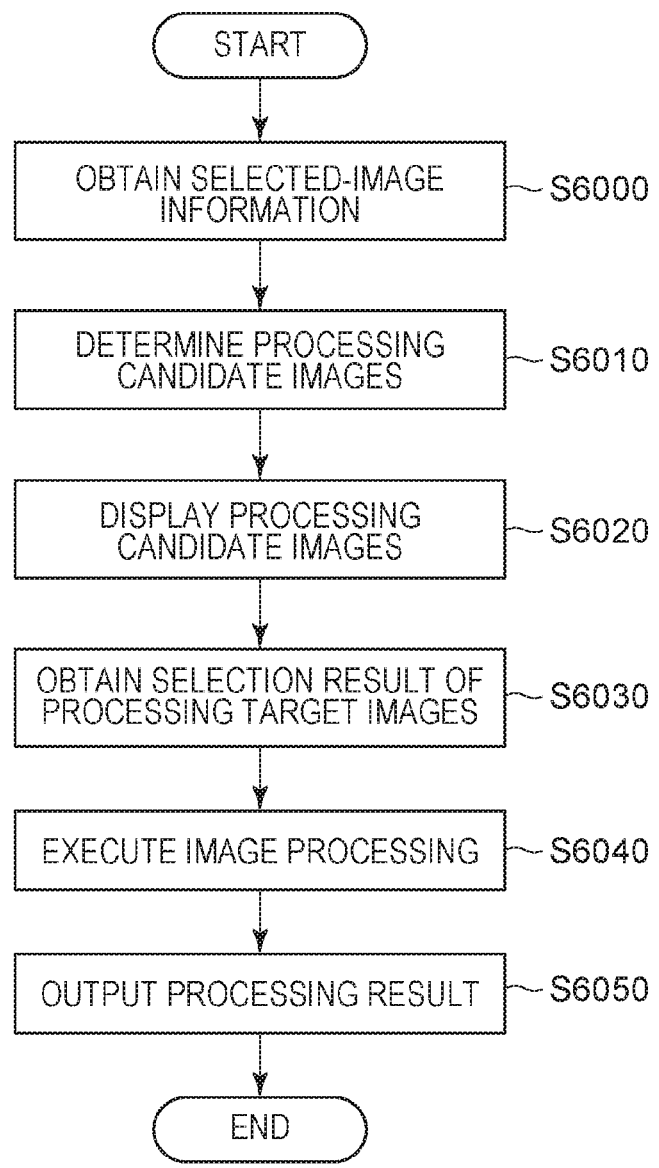
FIG. 6 is a flowchart illustrating the overall processing procedure in a third embodiment.

FIG. 6 is a flowchart illustrating the overall processing procedure of the image processing apparatus 100 in the present embodiment. Since steps S6020 to S6050 are the same as steps S3020 to S3050 of FIG. 3, respectively, descriptions thereof will be omitted.

(S6000) (Obtaining Selected-Image Information)

In step S6000, the data acquisition unit 210 obtains information on an image (group) selected by the operator via the selected-examination receiving unit 216. Suppose that the number of images (group) selected by the operator is any number equal to or greater than 1. The selected-image (group) information is temporarily stored in the RAM 103 in the image processing apparatus 100. In this step, the IDs of examinations to which the individual images belong are obtained in addition to the selected-image (group) information and are stored in the RAM 103.

(S6010) (Determining Processing Candidate Images)

In step S6010, the candidate determination unit 212 calculates an image candidate group that may be subjected to image processing using the selected-image information obtained in step S6000. How the image candidate group is calculated changes among cases: Case 1. the number of images specified in step S6000 is one; Case 2. the number is two or more and all of the images belong to the same examination; and Case 3. the number is two or more and the images belong to two or more examinations. A method for calculating the image candidate group will be specifically described hereinbelow.

First, in the case where the number of specified images is one, the candidate determination unit 212 searches the data server 200 for examinations whose attribute information, such as patient ID, modality type, and target site, matches the specified image. At that time, examinations to which the specified image belongs are excluded from the search target. The candidate determination unit 212 picks up all images that belong to the found examination (group) as a candidate image group. In other words, the candidate determination unit 212 corresponds to an example of the determination unit that determines, when one medical image is selected, the selected one medical image and one or a plurality of medical images obtained by searching based on the selected one medical image, as image processing candidate examinations.

Next, in the case where the number of specified images is two or more and all of the images belong to the same examination, the candidate determination unit 212 searches the data server 200 for examinations whose attribute information, such as patient ID, modality type, and target site, matches the specified two images. At that time, examinations to which the specified image belongs are excluded from the search target. The candidate determination unit 212 picks up all images that belong to the found examination (group) as a candidate image group. In other words, the candidate determination unit 212 corresponds to an example of a determination unit that, when a plurality of medical images that belong to the same examination are selected, determines, as image processing candidate examinations, the selected plurality of medical images and one or a plurality of medical images obtained by a search based on the selected plurality of medical images.

Lastly, in the case where the number of specified images is two or more and when the specified images belong to two or more examinations, the candidate determination unit 212 determines the specified image group as a candidate image group without searching the data server 200. An example of the case in which the specified images belong to two or more examinations is a case in which selected image A belongs to examination A, but selected image B belongs to examination B. In other words, the candidate determination unit 212 corresponds to an example of the determination unit that, when a plurality of medical images that belong to different examinations, determines the selected plurality of medical images as image processing candidate examinations.

As has been described in this step, the candidate determination unit 212 switches whether to search the data server 200 according to whether all of the images (group) specified by the operator belong to the same examination or belong to two or more examinations.

The processing of the image processing apparatus 100 is executed in that manner.

The present embodiment allows for providing a suitable image selecting function that reflects not only the operator's intention for examinations to "use this examination" but also the operator's intention for images to "use this image in this examination".

Other Embodiments

The present invention has an advantageous effect in that easy image selection that reflects the user's intention is possible.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
one or more memories storing instructions; and
one or more processors executing the instructions to:
receive a selection of one or more examinations to which a medical image belongs;
determine image processing candidate examinations based on a number of the selected one or more examinations;
display medical images belonging to the determined image processing candidate examinations on a display unit; and
execute image processing using, of the displayed medical images, a plurality of medical images selected by a user,
wherein, when the number of the selected one or more examinations is one, the one or more processors execute the instructions to determine the selected one examination and one or a plurality of examinations obtained by a search based on the selected one examination as the image processing candidate examinations, and
when the number of the selected one or more examinations is two or more, the one or more processors execute the instructions to determine the selected two or more examinations as the image processing candidate examinations.

2. The image processing apparatus according to claim 1, wherein, when the number of the selected one or more examinations is one, the one or more processors execute the instructions to make a search based on additional information on the selected one examination.

3. The image processing apparatus according to claim 1, wherein,
when the number of the selected one or more examinations is one, the one or more processors execute the instructions to:
determine the selected examination as a reference examination, and the one or plurality of examinations obtained by the search as comparative examination(s), and
display a medical image that belongs to the reference examination in a first display area on a screen and display a medical image that belongs to the comparative examination in a second display area on the screen.

4. The image processing apparatus according to claim 1, wherein,
when the number of the selected one or more examinations is two or more, the one or more processors execute the instructions to:
determine one of the selected two or more examinations as a reference examination, and determine an examination different from the one examination selected as the reference examination as a comparative examination, and
display a medical image that belongs to the reference examination in a first display area on a screen and display a medical image that belongs to the comparative examination in a second display area on the screen.

5. The image processing apparatus according to claim 1, wherein,
when the number of the selected one or more examinations is one, the one or more processors execute the instructions to:
determine the selected examination as a reference examination and determine one or a plurality of examinations obtained by the search as a comparative examination, and
when the number of the selected examination is two or more, the one or more processors execute the instructions to:
determine one of the selected two or more examinations as a reference examination and determine an examination different from the one examination selected as the reference examination as a comparative examination, and
display a medical image that belongs to the reference examination in a first display area on a screen and display a medical image that belongs to the comparative examination in a second display area on the screen.

6. The image processing apparatus according to claim 4, wherein, when the number of the selected one or more examinations is two or more, the one or more processors execute the instructions to:
determine a first selected examination of the selected two or more examinations as a reference examination.

7. The image processing apparatus according to claim 4, wherein, when the number of the selected two or more examinations is two or more, the one or more processors execute the instructions to:
determine, of the selected two or more examinations, an examination having an image capturing date and time closest to a current date and time as the reference examination.

8. The image processing apparatus according to claim 3, wherein the one or more processors execute the instructions to: display a medical image selected in the first display area in a third display area and display a medical image selected hi the second display area in a fourth display area.

9. A method for controlling an image processing apparatus, the method comprising:
receiving a selection of one or more examinations to which a medical image belongs;
determining image processing candidate examinations based on a number of the selected one or more examinations;
displaying medical images belonging to the determined image processing candidate examinations on a display unit; and
executing image processing using, of the displayed medical images, a plurality of medical images selected by a user,
wherein, when the number of the selected one or more examinations is one, in the determining, the selected one examination and one or a plurality of examinations obtained by a search based on the selected one examination are determined as the image processing candidate examinations, and
when the number of the selected one or more examinations is two or more, in the determining, the selected two or more examinations are determined as the image processing candidate examinations.

10. A non-transitory computer-readable storage medium storing a computer program for causing a computer to execute a method for controlling an image processing apparatus, the method comprising:
receiving a selection of one or more examinations to which a medical image belongs;
determining image processing candidate examinations based on a number of the selected one or more examinations;
displaying medical images belonging to the determined image processing candidate examinations on a display unit; and
executing image processing using, of the displayed medical images, a plurality of medical images selected by a user,
wherein, when the number of the selected one or more examinations is one, in the determining, the selected one examination and one or a plurality of examinations obtained by a search based on the selected one examination are determined as the image processing candidate examinations, and
when the number of the selected one or more examinations is two or more, in the determining, the selected two or more examinations are determined as the image processing candidate examinations.

* * * * *